United States Patent [19]

Farber et al.

[11] 4,388,250

[45] Jun. 14, 1983

[54] PROCESS FOR THE PREPARATION OF P-HYDROXY-BENZYL-NITRILES AND CORRESPONDING AMINES

[75] Inventors: Leon Farber, Somerset; Peter S. Gradeff, Pottersville, both of N.J.

[73] Assignee: Rhone Poulenc Inc., Monmouth Junction, N.J.

[21] Appl. No.: 358,397

[22] Filed: Mar. 15, 1982

[51] Int. Cl.$^3$ .................... C07C 121/75; C07C 87/28
[52] U.S. Cl. ................. 260/465 F; 564/389; 564/390
[58] Field of Search ............... 260/465 F; 564/389, 564/390, 397

[56] References Cited

U.S. PATENT DOCUMENTS

| | | | |
|---|---|---|---|
| 3,983,160 | 9/1976 | Meyer | 260/465 F |
| 4,154,757 | 5/1979 | Cooper et al. | 260/465 F |
| 4,154,758 | 5/1979 | McMenim | 260/465 F |

FOREIGN PATENT DOCUMENTS 1067099  11/1979  Canada .

OTHER PUBLICATIONS

Short et al., *Tetrahedra*, vol. 29, 1931, (1973).
Haskelberg, *J. Am. Chem. Soc.*, vol. 70, 2811, (1948).
Emerson, *Organic Reactions*, vol. 4 (III), p. 174, (1948).
Winans, *J. Am. Chem. Soc.*, vol. 61, 3566, (1939).
Alexander et al., *J. Am. Chem. Soc.*, vol. 70, 1315, (1948).

*Primary Examiner*—Dolph H. Torrence

[57] ABSTRACT

A process is provided for the preparation of p-hydroxy-benzyl-nitriles starting from the corresponding p-hydroxy-benzaldehyde, first reducing the p-hydroxy-benzaldehyde to the p-hydroxy-benzyl amine, a primary amine, with hydrogen in the presence of aqueous ammonia, preferably with the addition of small amounts of lower alkyl alcohol; and Raney nickel catalyst at low pressure; and then converting the amine to the p-hydroxy-benzyl-nitrile by reaction with sodium cyanide at elevated temperature; the first stage, the reduction, is applicable also to o- and m-hydroxy benzaldehydes.

19 Claims, No Drawings

PROCESS FOR THE PREPARATION OF P-HYDROXY-BENZYL-NITRILES AND CORRESPONDING AMINES p-Hydroxy-benzyl nitrile has been prepared by various routes, none entirely satisfactory, and all using relatively expensive starting materials and/or reagents.

U.S. Pat. No. 4,154,757 patented May 15, 1979 to Cooper, Edwards and Copeland reacts p-hydroxy-mandelic acid with cyanide ion, conveniently in the form of an alkali metal cyanide such as potassium or sodium cyanide, in solution in a relatively high-boiling dipolar aprotic solvent such as N,N-dimethylformamide, at a temperature between 120° and 190° C., optionally in the presence of a base. The p-hydroxy-mandelic acid starting material is obtained in the form of sodium or potassium p-hydroxymandelate monohydrate, using this procedure.

U.S. Pat. No. 4,154,758 patented May 15, 1979 to McMenim reacts p-hydroxy-phenylglycine acid with cyanide ion, conveniently in the form of an alkali metal cyanide such as sodium or potassium cyanide, in solution in a relatively high boiling dipolar aprotic solvent such as N,N-dimethylformamide, at a temperature between 100° and 250° C.

While these procedures give good yields, each of the starting materials is costly, and not commercially available in large quantities, but has to be especially prepared.

U.S. Pat. No. 3,983,160, patented Sept. 28, 1976, Offenlegungsschrift No. 2,457,079, to Horst Meyer, prepares an ortho or para hydroxy phenylacetonitrile of the formula:

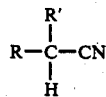

wherein

R is ortho or parahydroxyphenyl, further unsubstituted or further substituted by one or two substituents independently selected from the group consisting of lower alkyl or lower alkoxy and R' is hydrogen, lower alkyl, phenyl or carbo(lower alkoxy), which comprises allowing the corresponding ortho or parahydroxybenzyl alcohol of the formula:

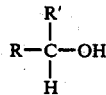

to react with hydrogen cyanide in the presence of a diluent at a temperature of from about 80° to about 190° C.

Another procedure described by Short, Dunnigan and Ours *Tetrahedron* 29 1931 (1973), for the preparation of the benzylamines is by way of the Mannich reaction on the corresponding phenols. Short et al also describe the reaction of N-methyl vanillylamine with potassium cyanide to form the corresponding benzyl cyanide, according to the following reaction:

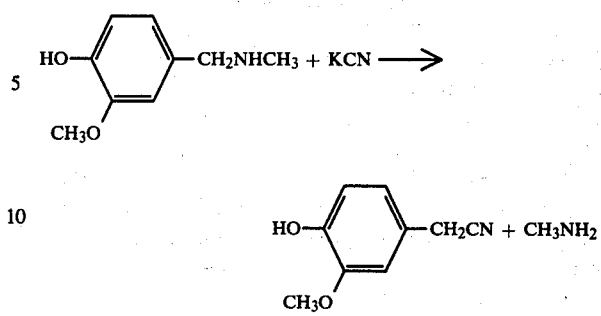

Short et al also prepared phenyl acetonitriles from benzylamines by dissolving the amine in dimethylformamide, and adding potassium cyanide. The mixture was stirred and heated at elevated temperature under nitrogen, acidified, and dissolved and evaporated to recover the nitrile.

Haskelberg *J. Am. Chem. Soc.* 70 2811 (1948) describes an aminative hydrogenation to convert ketones to primary amines, using ethanolic ammonia, hydrogen at atmospheric pressure, and Raney nickel. In most cases, a secondary amine was also obtained as a byproduct.

Emerson *Organic Reactions* Vol. 4, Chapter 3, p. 174 (1948) notes that benzaldehyde is converted to benzylamine in good yield by the hydrogenation of benzaldehyde in the presence of an equimolar quantity of ammonia, using ethanol as the solvent and with Raney nickel catalyst at pressures of from 20 to 150 atmospheres. A small amount of dibenzylamine is also formed, but easily separated because of the wide difference in boiling points of the two products. Reference is made to the work by Winans *J. Am. Chem. Soc.* 61 3566 (1939). It is however stated that only a few other aromatic aldehydes have been converted to primary amines by reductive alkylation. Tolualdehyde has been converted to the primary amine in good yield, and so has ortho-chlorobenzaldehyde, as shown by Winans. Aldehydes containing other aromatic nuclei have apparently not been used in the reaction.

Emerson notes that the hydrogenation of an ethanolic solution of ammonia and the aldehyde in the presence of Raney nickel catalyst has proved most effective. The ammonia is used in excess to minimize secondary amine formation. The best results have been achieved with hydrogen at pressures of 20 to 150 atmospheres. At pressures below 20 atmospheres, the hydrogenation is too slow for convenience. Moreover, a temperature of at least 40° C. is said to be necessary for the reaction to start, and good results have been obtained at from 40° to 150° C.

Alexander and Misegades *J. Am. Chem. Soc.* 70 1315(1948) describe a low pressure reductive alkylation method for the conversion of ketones to primary amines. In their summary of the literature, they state that carbonyl compounds are known to be hydrogenated in the presence of ammonia to produce mixtures of primary, secondary, and tertiary amines. Originally, the reaction was carried out by the hydrogenation of the carbonyl compound in ethanol, saturated with ammonia at low pressure over a nickel catalyst. Better yields and more reproducible results, however, have been obtained over Raney nickel, under hydrogen pressures of 20 to 150 atmospheres at temperatures of from 40° to 150° C., with reference to Mignonac Compt. Rend. 172 223 (1921); Schwoegler and Adkins J. Am. Chem. Soc. 61 3499 (1939); Winans J. Am. Chem. Soc. 61 3566 (1939).

Since high pressure apparatus is not always available, Alexander and Misegades tried to improve on Mignonac's low pressure reductive alkylation reaction using methanol saturated with ammonia over a platinum oxide catalyst. In addition to several ketones, isobutyraldehyde and benzaldehyde were also subjected to reductive amination in the presence of ammonium chloride. The yields were rather poor, 10% and 15%, respectively, in contrast to the ketone yields, which were considerably better, ranging to as high as 69% in the case of acetophenone.

Winans himself indicates that hydrogen pressures as low as 20 atmospheres have been satisfactory, but that higher pressures up to 100 atmospheres were generally used, at temperatures of from 40° to 75° C. The ammonia was added as a standard alcoholic solution.

Niuchi, Azagami, Hirota, Nakarai and Kageyama, Japanese Pat. No. 17,730 of 1967, prepared vanillylamine by reaction of vanillin with liquid ammonia in the presence of Raney nickel catalyst at 40° to 70° C. under 100 atmospheres hydrogen pressure, heating the mixture for six hours.

Podesva and Iera, Canadian Pat. No. 1,067,099, patented Nov. 27, 1979, commenting on the Short et al article in Tetrahedron and Offenlegungsschrift No. 2,457,079, prepare 3-lower alkoxy-4-hydroxy-benzyl cyanides by reaction of an N-phenyl-3-lower alkoxy-4-hydroxy benzylamine of the formula

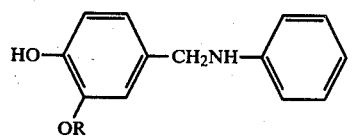

II where R is lower alkyl with an alkali metal cyanide in a polar solvent such as dimethylformamide at 100° to 150° C. The N-phenyl-3-lower alkoxy-4-hydroxy-benzylamine is prepared by the following synthesis:

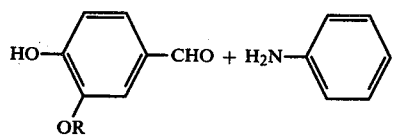

III

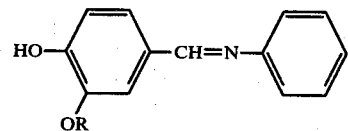

IV

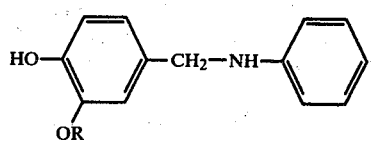

II

The reduction is carried out at low ambient temperature using a metal hydride such as sodium borohydride, which is a very expensive alternative to hydrogen.

In accordance with the present invention, a two-stage synthesis is provided for preparing p-hydroxy-benzyl nitriles which comprises, in sequence:

(a) reducing a benzaldehyde having the formula:

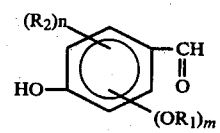

wherein:
$R_1$ is methyl or ethyl;
$R_2$ is methyl or ethyl;
m is a number from 0 to 4;
n is a number from 0 to 4;
with hydrogen gas at a pressure within the range from atmospheric pressure up to about 150 psi at a temperature within the range from about 20° to about 100° C. in an aqueous reaction medium comprising ammonia in an amount within the range from a stoichiometric amount up to about ten times the stoichiometric amount and Raney nickel catalyst, thereby forming the corresponding benzyl amine:

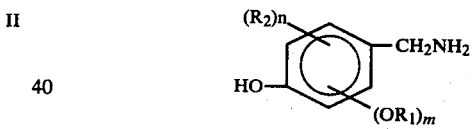

(b) replacing the amino group of the benzylamine with a nitrile group by reaction with a cyanide selected from the group consisting of alkali metal cyanides and hydrogen cyanide in solution in a solvent selected from the group consisting of dimethyl formamide, dimethyl sulfoxide and dimethyl pyrrolidone at a temperature within the range from about 80° C. up to the reflux temperature of the solution, thereby forming the corresponding benzyl nitrile:

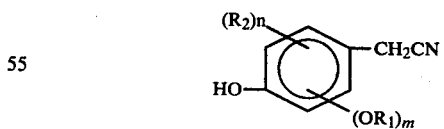

and (c) removing the solvent and recovering the benzyl cyanide.

The first stage of this synthesis, the reductive amination of hydroxy-benzaldehyde with aqueous ammonia at low pressure, is novel, and is applicable not only to p-hydroxy-benzaldehyde, never converted before to p-hydroxy-benzylamine by reductive amination, but also to o- and m-hydroxy-benzaldehydes. The second stage of the reaction proceeds with only p-hydroxybenzylamines. Hence, the two-stage synthesis is limited to the reaction of p-hydroxy-benzaldehydes. If however the benzylamine is not to be converted to the corresponding nitrile, the first stage of the process can be applied also to the o- and m-hydroxy-benzaldehydes.

Thus, in accordance with the invention, a synthesis also is provided for preparing primary hydroxy-benzyl amines which comprises (a) reducing a benzaldehyde having the formula:

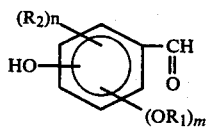

wherein:
HO is in the ortho, meta, or para position;
$R_1$ is methyl or ethyl;
$R_2$ is methyl or ethyl;
m is a number from 0 to 4;
n is a number from 0 to 4;
with hydrogen gas at a pressure within the range from atmospheric pressure up to about 150 psi at a temperature within the range from about 20° to about 100° C. in an aqueous reaction medium comprising ammonia in an amount within the range from a stoichiometric amount up to about ten times the stoichiometric amount and Raney nickel catalyst, thereby forming the corresponding benzyl amine:

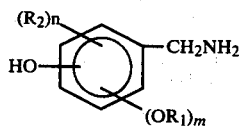

and (b) recovering the benzyl amine.

The reaction medium in the first stage reaction is an aqueous system in which the reacting aldehyde may or may not become completely dissolved in the aqueous phase at the beginning of the reaction. The reaction product, the corresponding benzylamine, is insoluble in the reaction mixture and therefore precipitates out as the reaction proceeds.

As the amount of benzylamine precipitate increases, so does the viscosity of the reaction mixture. In order to keep the mixture workable, it may be desirable to add more water, so necessary, to reduce viscosity, or, alternatively, a water miscible lower aliphatic alcohol such as methanol or ethanol as a diluent to reduce viscosity. The lower alkanol does not however take part in the reaction, but only serves to reduce viscosity.

While the process is applicable to any p-hydroxy-benzaldehyde, it is particularly of interest commercially applied to p-hydroxybenzaldehyde and vanillin, which is 3-methoxy-4-hydroxy-benzaldehyde.

Surprisingly, the reaction does not require high hydrogen pressures. The reaction proceeds very slowly at atmospheric pressure. Thus, there is reason to use a superatmospheric pressure, and, if desired, pressures up to about 150 psi can be used. The preferred range for hydrogen pressure is from atmospheric up to about 75 psi.

Thus it is possible to carry out the reaction in a closed vessel, pressurized with the amount of hydrogen required for the reductive amination, permitting the pressure in the vessel to reach whatever maximum it will at the reaction temperature selected.

The reaction proceeds at room temperature, and thus there is no reason to use a higher temperature, although the reaction does proceed more rapidly at elevated temperatures. Temperatures up to about 100° C. can easily be employed. Somewhat higher temperatures can be used if the hydrogen pressure is maintained well above atmospheric pressure.

Ammonia is of course required at least in stoichiometric amount to form the primary amino group $-NH_2$. It has been found desirable to use an excess, to ensure completion of the reaction. A considerable excess can be used, up to about 10 moles, if desired, although this is not necessary. Preferably, however, the amount of ammonia is within the range from the stoichiometric amount, i.e., 1 mole per mole of benzaldehyde up to 5 moles.

The amount of Raney nickel catalyst is in no way critical. The reaction proceeds with amounts as small as 1% by weight of the reaction mixture. While much higher amounts, up to about 25% by weight of the reaction mixture can be used, such larger amounts are really not required, and may be wasteful. The preferred amount is within the range from 5% to 10% by weight of the reaction mixture.

The second stage of the reaction has been applied by J. H. Short, D. A. Dunnigan and C. W. Ours, *Tetrahedron* 29 1934 (1973) who reported that 4-hydroxy-3-methoxybenzylamine (vanillylamine), its N-Me and its N,N-dimethyl derivatives gave rise to 4-hydroxy-3-methoxyphenylacetonitrile in 64%, 58%, and 56% yield, respectively.

An OH group in the meta position failed to promote this reaction. None of the corresponding nitrile was isolated when 3-hydroxy-4-methoxybenzylamine (isovanillylamine) was allowed to react with cyanide ion in the usual manner. The only product isolated was the transamidation product, N-(3-hydroxy-4-methoxybenzyl)formamide.

The second stage of the reaction is straightforward, and is best carried out in solution in an inert organic solvent, of which dimethyl formamide, dimethyl sulfoxide and dimethyl pyrrolidone are preferred. The amount of solvent is not critical, and can be within the range from about 300 to about 2000 g/mole and preferably from about 500 to about 1200 g/mole of the hydroxy benzylamine. While larger amounts of solvent can be used, the process then becomes uneconomic.

The reaction temperature is moderate, within the range from about 80° C. to the reflux temperature of the solvent used. At the conclusion of the reaction, the solvent is stripped off at reduced pressure and low temperature. The benzyl nitrile can then be taken up in acidified water, and the aqueous mixture extracted with methyl isobutyl ketone or isopropyl ether.

The following Examples in the opinion of the inventors represent preferred embodiments of the invention:

EXAMPLES 1 to 8

Eight reactions were run, using the following procedure:

In a 500 cc reaction flask of a shaker-type hydrogenator was placed the amount of p-hydroxy-benzaldehyde, aqueous ammonium hydroxide, methanol and Raney nickel catalyst shown for each Example in Table I below, and the air in the vessel then displaced with hydrogen at atmospheric pressure. The vessel was closed, and the reductive amination reaction then carried out at the temperature indicated in the Table, for the reaction time shown. At the conclusion of the reaction, in Examples, 1, 3, 5, 6, 7, and 8, yield was determined by gas chromatographic analysis. The following results were obtained:

TABLE I

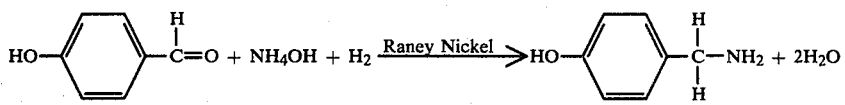

| Example No. | PHB[1] | Mole Ratios NH4OH (Aq) (M.R./% NH3) | CH3OH (ml) | RaNi (g) | Time (hours) | Temp. (°C.) | Yield (%) | Remarks |
|---|---|---|---|---|---|---|---|---|
| 1 | 1 | 5.0/25.7% | 500 | 10 | 6.5 | Ambient | Virtually quantitative | |
| 2 | 1 | 2.0/25.7% | 500 | 10 | 9.5 | Ambient | | Reduction slow. Byproducts formed. 85% pure by GC |
| 3 | 1 | 5.0/25.7% | 250 | 10 | 7 | Ambient | 96.9 | |
| 4 | 1 | 5.0/25.7% | 0 | 10 | 6 | 24–35 | | H2 uptake only 75% of theory. Reaction mixture became very viscous and reaction was stopped at six hours. |
| 5 | 1 | 5.0/24.2% | 0 (500 ml H2O) | 11.7 | 23 | Ambient | 98.3 | |
| 6 | 1 | 5.0/25.7% | 250 | 10 | 7 | Ambient | 97.6 | Same conditions as Example 3. A desiccator was used to dry the product. |
| 7 | 1 | 5.1/23.0% | 500 | 10 | 4 | 22.5 to 55.0 | 91.5 | |
| 8 | 1 | 5.0/NH3 GAS | 847.5 | 5 | 25.5 | 20 to 43 | 92.9 | Ammonia gas was used. Reaction was run under anhydrous conditions. |

[1]PHB = p-hydroxy-benzaldehyde

EXAMPLES 9 to 13

In procedures similar to that described for Examples 1 to 8, vanillylamine (4-hydroxy-3-methoxybenzylamine), o-vanillylamine (2-hydroxy-3-methoxybenzylamine), salicylamine (2-hydroxybenzylamine) and 3-hydroxybenzylamine were prepared from the corresponding benzaldehydes. As shown in Table II, the following results were obtained:

TABLE II

| Example No. | Hydroxy benzaldehyde | Aldehyde | MOLE RATIOS NH4OH(Aq.) (M.R./% NH3) | CH3OH (Ml) | RaNi Wet(g) | Time (hours) | Temp. (°C.) | Yield % | Remarks |
|---|---|---|---|---|---|---|---|---|---|
| 9 | 3-OCH3 4-OH | 1 | 5/24.2% | 500 | 47 | 3 | 28 to 37 | 96.1 | Vanillylamine |
| 10 | 2-OH 3-OCH3 | 1 | 5/29.6% | 560 | 26.7 | 5 | 22 to 42 | 93.1 | o-Vanillylamine |
| 11 | 2-OH | 1 | 5/24.2% | 667 | 26.7 | 7 | 27 to 42 | 92.9 | Salicylamine |
| 12 | 2-OH | 1 | 5/NH3 Gas | 583 | 11.7 | 23 | 20 to 42 | 91.5 | Salicylamine |
| 13 | 3-OH | 1 | 5/24.2% | 250 | 26.7 | 3 | Ambient | 92.7 | 3-Hydroxybenzyl-amine |

EXAMPLES 14 to 18

The p-hydroxy-benzylamine obtained as a reaction product in Example 9 by the above reaction was then separated into five portions and each portion reacted with sodium cyanide in the molar proportions and under the reaction conditions shown in Table III below, carrying out the reaction in a reaction vessel equipped with a stirrer and heating path at atmospheric pressure. The results obtained are shown in Table III.

TABLE III

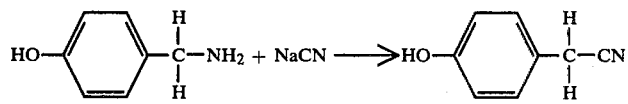

| Example No. | Mole Ratios PHBAM[1] | NaCN | Solvent (Ml/Ml) | Time (hours) | Temp. (°C.) | Yield % | Remarks |
|---|---|---|---|---|---|---|---|
| 14 | 1 | 1.26 | DMF (1140) | 8 | 120 | 76.1 | In determining yields analysis of the distilled products are not included. Most of the analytical determinations ranged from 97 to 99% purity. |
| 15 | 1 | 1.1 | DMF (1000) | 6 | 120 | 80.5 | In the work-up, MIBK was used in place of IPE, as the extractant, and sulfuric acid in place of acetic acid. |

TABLE III-continued

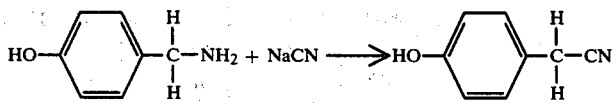

| | Mole Ratios | | | | | | |
|---|---|---|---|---|---|---|---|
| Example No. | PHBAM[1] | NaCN | Solvent (Ml/Ml) | Time (hours) | Temp. (°C.) | Yield % | Remarks |
| 16 | 1 | 1.1 | DMF (1082.7) | 3 | 140 | 68.8 | The yield is based on the distillation of only 10.22 g crude. |
| 17 | 1 | 1.1 | DMF (570.5) | 3 | 140 | 66.9 | |
| 18 | 1 | 1.1 | DMF (571) | 3 | 120 | 68.8 | |

[1]p-hydroxy benzylamine. Reaction product was p-hydroxy benzyl nitrile.

EXAMPLE 19

To 1 mole of vanillylamine was added, with mixing, 1.1 moles sodium cyanide and 1 liter dimethylformamide. The mixture was heated with stirring at a temperature of 120° C. for fifteen hours. An argon atmosphere was used throughout. After work-up, a yield of 79.7% of the distilled vanillylnitrile was afforded.

Having regard to the foregoing disclosure, the following is claimed as the inventive and patentable embodiments thereof:

1. A process for preparing p-hydroxy-benzyl nitriles which comprises, in sequence:

(a) reducing a benzaldehyde having the formula:

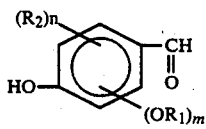

wherein:
$R_1$ is methyl or ethyl;
$R_2$ is methyl or ethyl;
m is a number from 0 to 4;
n is a number from 0 to 4;
with hydrogen gas at a pressure within the range from atmospheric pressure up to about 150 psi at a temperature within the range from about 20° to about 100° C. in an aqueous reaction medium comprising ammonia in an amount within the range from a stoichiometric amount up to about ten times the stoichiometric amount and Raney nickel catalyst, thereby forming the corresponding benzyl amine:

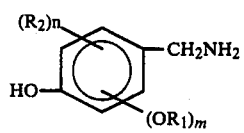

(b) replacing the amino group of the benzylamine with a nitrile group by reaction with a cyanide selected from the group consisting of alkali metal cyanides and hydrogen cyanide in solution in a solvent selected from the group consisting of dimethyl formamide, dimethyl sulfoxide and dimethyl pyrrolidone at a temperature within the range from about 80° C. up to the reflux temperature of the solution, thereby forming the corresponding benzyl nitrile:

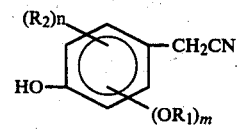

and (c) removing the solvent and recovering the benzyl cyanide.

2. A process according to claim 1 in which the benzaldehyde is p-hydroxy-benzaldehyde.

3. A process according to claim 1 in which the benzaldehyde is 3-methoxy-4-hydroxy-benzaldehyde.

4. A process according to claim 1 in which the hydrogen pressure is within the range from atmospheric pressure up to about 75 psi.

5. A process according to claim 1 in which the reaction is carried out in a closed vessel, pressurized with the amount of hydrogen required for the reductive amination, permitting the pressure in the vessel to reach whatever maximum it will at the reaction temperature selected.

6. A process according to claim 1 in which the reaction temperature is room temperature.

7. A process according to claim 1 in which the amount of ammonia is within the range from 1 mole to 5 moles per mole of benzaldehyde.

8. A process according to claim 1 in which the amount of Raney nickel catalyst is within the range from 1% up to about 25% by weight of the reaction mixture.

9. A process according to claim 1 in which in stage (b) the amount of solvent is within the range from about 300 to about 2000 g/mole of benzylamine.

10. A process according to claim 1 in which in stage (c) the solvent is stripped off at reduced pressure and low temperature, the benzyl nitrile is taken up in acidified water, and the aqueous mixture extracted with methyl isobutyl ketone or isopropyl ether.

11. A process for preparing primary hydroxy-benzyl amines which comprises (a) reducing a benzaldehyde having the formula:

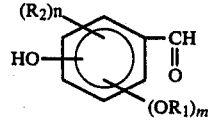

wherein:

HO is in the ortho, meta or para position;
$R_1$ is methyl or ethyl;
$R_2$ is methyl or ethyl;
m is a number from 0 to 4;
n is a number from 0 to 4;
with hydrogen gas at a pressure within the range from atmospheric pressure up to about 150 psi at a temperature within the range from about 20° to about 100° C. in an aqueous reaction medium comprising ammonia in an amount within the range from a stoichiometric amount up to about ten times the stoichiometric amount and Raney nickel catalyst, thereby forming the corresponding hydroxy-benzylamine:

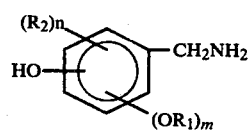

and
(b) recovering the hydroxy-benzylamine.

12. A process according to claim 11 in which the HO is in the para position.

13. A process according to claim 11 in which the HO is in the ortho position.

14. A process according to claim 11 in which the HO is in the meta position.

15. A process according to claim 11 in which the hydrogen pressure is within the range from atmospheric pressure up to about 75 psi.

16. A process according to claim 11 in which the reaction is carried out in a closed vessel, pressurized with the amount of hydrogen required for the reductive amination, permitting the pressure in the vessel to reach whatever maximum it will at the reaction temperature selected.

17. A process according to claim 11 in which the reaction temperature is room temperature.

18. A process according to claim 11 in which the amount of ammonia is within the range from 1 mole to 5 moles per mole of benzaldehyde.

19. A process according to claim 11 in which the amount of Raney nickel catalyst is within the range from 1% up to about 25% by weight of the reaction mixture.

* * * * *